(12) United States Patent
Perrotti et al.

(10) Patent No.: US 9,220,706 B2
(45) Date of Patent: Dec. 29, 2015

(54) INHIBITION OF LEUKEMIC STEM CELLS BY PP2A ACTIVATING AGENTS

(71) Applicant: Ohio State Innovation Foundation, Columbus, OH (US)

(72) Inventors: Danilo Perrotti, Dublin, OH (US); Paolo Neviani, Columbus, OH (US)

(73) Assignees: NATIONAL INSTITUTES OF HEALTH (NIH), Bethesda, MD (US); U.S. DEPT. OF HEALTH AND HUMAN SERVICES (DHHS), Bethesda, MD (US); THE UNITED STATES OF AMERICA NIH DIVISION OF EXTRAMURAL INVENTIONS AND TECHNOLOGY RESOURCES (DEITR), Washington, DC (US)

( * ) Notice: Subject to any disclaimer, the term of this patent is extended or adjusted under 35 U.S.C. 154(b) by 0 days.

(21) Appl. No.: 14/404,496

(22) PCT Filed: May 31, 2013

(86) PCT No.: PCT/US2013/043521
§ 371 (c)(1),
(2) Date: Nov. 28, 2014

(87) PCT Pub. No.: WO2013/181488
PCT Pub. Date: Dec. 5, 2013

(65) Prior Publication Data
US 2015/0141502 A1    May 21, 2015

Related U.S. Application Data

(60) Provisional application No. 61/654,267, filed on Jun. 1, 2012.

(51) Int. Cl.
*A61K 31/137* (2006.01)
*A61K 31/353* (2006.01)

(52) U.S. Cl.
CPC ............ *A61K 31/353* (2013.01); *A61K 31/137* (2013.01)

(58) Field of Classification Search
CPC .................................................. A61K 31/137
USPC ................................................. 514/649, 653
See application file for complete search history.

(56) References Cited

U.S. PATENT DOCUMENTS

| | | | |
|---|---|---|---|
| 5,948,820 A | 9/1999 | Fujita et al. | |
| 7,838,562 B2* | 11/2010 | Hla et al. | 514/646 |
| 8,362,071 B2* | 1/2013 | Chen et al. | 514/458 |
| 8,633,161 B2* | 1/2014 | Perrotti et al. | 514/19.6 |
| 2010/0267673 A1 | 10/2010 | Chen et al. | |
| 2010/0267820 A1 | 10/2010 | Chen et al. | |
| 2011/0105437 A1 | 5/2011 | Ralph et al. | |

FOREIGN PATENT DOCUMENTS

| | | |
|---|---|---|
| WO | 9610634 | 4/1995 |
| WO | 2011038467 | 4/2011 |

OTHER PUBLICATIONS

International Search Report for PCT/US2013/043521, dated Feb. 4, 2014, 1 page.

* cited by examiner

*Primary Examiner* — Golam M M Shameem
(74) *Attorney, Agent, or Firm* — Tarolli, Sundheim, Covell & Tummino LLP

(57) ABSTRACT

A method of inhibiting the growth of leukemic hematopoietic stem cells in a subject with leukemia is described. The method includes administering a therapeutically effective amount of a composition including a compound of formula I: I wherein $R^1$ is independently selected from hydrogen and methyl; $R^2$ is selected from the group consisting of 4,8-dimethyl-non-1-enyl, 4,8-dimethyl-nonyl, non-1-enyl, and nonanyl groups; X is a carboxyl, phosphonic, or sulfonic moiety, and n is an integer from 1 to 6, or a compound of Formula II: II wherein $R^1$ is a $C_6$-$C_{12}$ alkyl or $C_6$-$C_{12}$ alkoxy group; $R^2$ is independently selected from the group consisting of hydrogen, methoxy, and hydroxyl; and $R^3$ is an alkyl or cycloalkyl group; or a pharmaceutically acceptable salt thereof.

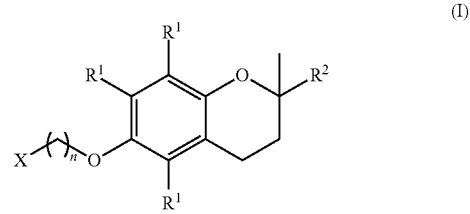

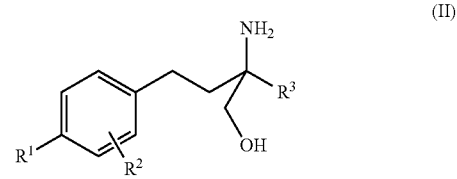

11 Claims, 6 Drawing Sheets

INHIBITION OF LEUKEMIC STEM CELLS BY PP2A ACTIVATING AGENTS

CROSS-REFERENCE TO RELATED APPLICATIONS

This application is the U.S. national phase entry of PCT/US2013/043521, with an international filing date of May 31, 2013, which claims priority to and the benefit of U.S. provisional patent application No. 61/654,267, filed on Jun. 1, 2012, the contents of which are hereby incorporated by reference in their entirety.

GOVERNMENT FUNDING

The present invention was supported by the Leukemia and Lymphoma Society grant 1077-08 and National Institutes of Health grant R01 CA095512. The Government has certain rights in this invention.

BACKGROUND

Chronic myeloid leukemia (CML) is a hematopoietic stem cell (HSC)-derived and progenitor-driven myeloproliferative disorder that may progress from a manageable chronic phase to an incurable blastic phase. Perrotti et al., J Clin Invest; 120: 2254-64 (2010). BCR-ABL1 is a tyrosine kinase whose constitutive activity in hematopoietic progenitors is essential for CML emergence, maintenance and progression. Most CML patients undergoing tyrosine kinase inhibitor (TKI) monotherapy achieve major or complete molecular response (CMR) with low risk of relapse or progression. However, only a few patients in CMR remain disease-free after TKI (e.g. imatinib) discontinuation. Rousselot et al., Blood 109: 58-60 (2007). Persistence of cells from the original BCR-ABL1$^+$ clone in TKI-treated but not in allogeneic transplanted patients in CMR suggests the existence of non-proliferating (quiescent) Ph$^+$ HSCs with innate TKI resistance, and for which BCR-ABL1 kinase activity appears dispensable. Pellicano et al., Current hematologic malignancy reports, 6: 82-7 (2011). However, how these cells persist in TKI responsive patients, and whether BCR-ABL1 expression is required for their survival/self-renewal remain unknown. Seemingly, the safety and clinical benefit of various approaches envisioning the direct killing or the induction of these Ph$^+$ HSCs into cell-cycle as a mechanism to restore TKI sensitivity is as yet uncertain.

FTY720 (Fingolimod/Gilenya™) is an oral sphingosine analog used in multiple sclerosis (MS) patients because it acts as a reversible immunosuppressant when, upon phosphorylation, is internalized by the sphingosine-1-phosphate receptor (S1PR1). FTY720 also has a strong anticancer activity that does not require phosphorylation or S1PR1 interaction but depends on restoration of PP2A function. Neviani et al., J Clin Invest, 117: 2408-21 (2007); Roberts et al. Cancer Res; 70: 5438-47 (2010). In Ph$^+$ leukemias, FTY720-induced PP2A activity promotes BCR-ABL1 inactivation/degradation and inhibition of survival factors (e.g. JAK2, Akt and ERK1/2). Neviani et al. Cancer Cell, 8: 355-68 (2005). This results in apoptosis of CD34$^+$ progenitors from TKI-sensitive and -resistant Ph$^+$ patients but not from healthy individuals, which already harbor highly active PP2A, and ultimately translates into long-term survival with normal myelopoiesis and absence of toxicity in BCR-ABL1$^+$ leukemic mice.

The success of tyrosine kinase inhibitors depends on the addiction of Philadelphia-positive (Ph$^+$) CML progenitors to BCR-ABL1 kinase activity. However, CML quiescent HSCs are TKI-resistant and represent an active disease reservoir. Accordingly, there is a need for compounds able to treat TKI-resistant leukemic hematopoietic stem cells.

SUMMARY OF THE INVENTION

Herein the inventors show that BCR-ABL1 expression but not activity is important in Ph+ quiescent HSCs for JAK2 activation that, in turn, enhances β-catenin activity and induces SET-mediated inactivation of protein phosphatase 2A (PP2A), a tumor suppressor whose lost activity in cancer, including CML, can be pharmacologically restored. The protein SET (I2PP2A/TAF-Iβ) is a potent protein phosphatase 2A (PP2A) inhibitor that has been implicated in many cell processes such as DNA replication, chromatin remodeling, gene transcription, differentiation, migration, and cell-cycle regulation.

The inventors showed here that restoration of PP2A activity by FTY720 or its non-immunosuppressive derivatives (S)-FTY720-OMe, (S)-FTY720-regioisomer and OSU-2S selectively suppresses survival of Ph$^+$ but not normal quiescent HSCs. Mechanistically, FTY720 disrupts the SET-PP2A interaction, thereby allowing PP2A activation, which inhibits JAK2 and impairs β-catenin-dependent survival through GSK3β activation. These findings bring CML therapy further into a setting where patients are brought into CMR by TKIs and possibly cured by FTY720 or its derivatives.

BRIEF DESCRIPTION OF THE FIGURES

The present invention may be more readily understood by reference to the following drawings.

DETAILED DESCRIPTION OF THE INVENTION

Figure 1:
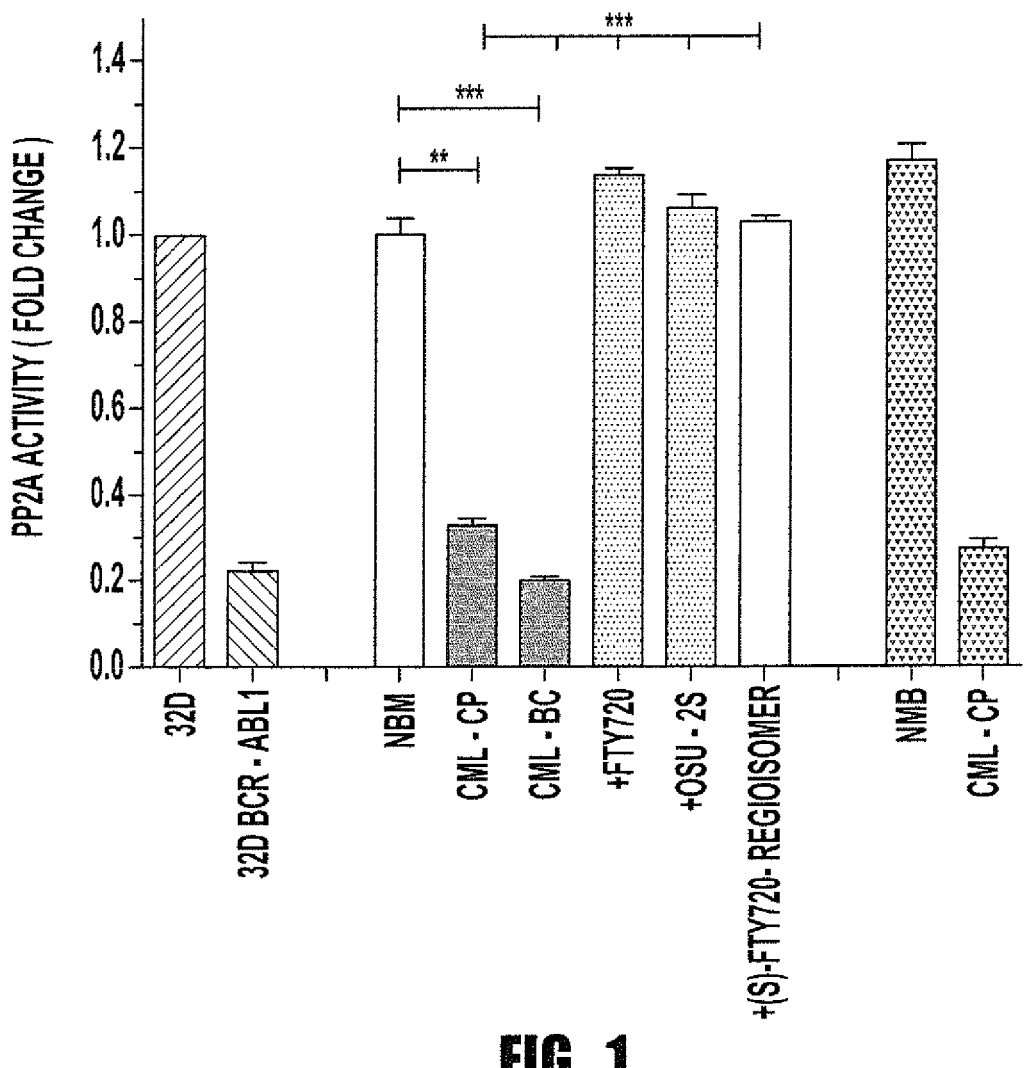
FIG. 1 provides a bar graph showing PP2A activity is inhibited in CML HSCs. A PP2A phosphatase assay (Mean±SD) in CD34$^+$/CD38$^-$ and CD34$^+$/CD38$^+$ cell fractions from BM of healthy (NBM) and CML donors; 32Dcl3 and 32D-BCR-ABL cells were used as controls.

A method of inhibiting the growth of leukemic hematopoietic stem cells in a subject with leukemia using FTY720-derived PP2A activating compounds is described. The compounds have been shown to be able to selectively suppress the survival of leukemic but not normal quiescent hematopoietic stem cells as a result of selective inactivation of BCR-ABL1 and other survival factors in leukemic stem cells.

Definitions

The terminology as set forth herein is for description of the embodiments only and should not be construed as limiting of the invention as a whole. As used in the description of the invention and the appended claims, the singular forms "a". "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is a an aryl group that is attached to the remainder of the structure by an intervening alkyl group, whereas an aralkyl group is an aryl group that is attached directly to the structure but that includes one or more additional alkyl groups attached thereto. In the context of the present invention, suitable organic groups for the compounds of the invention are those that do not interfere with the desired activity of the compounds (e.g., their anticancer activity). In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 12 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alley groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclobutyl, cyclobutylmethyl, cyclopentyl, and cyclohexyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with one or more nonperoxidic O, N, S, or F substituents or other conventional substituents such as methyl groups. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. This is true regardless of whether or not the enantiomers are shown in chemical formula representing the compounds. For example, if a compound that includes a chiral center is shown without any indication of stereochemistry, it is presumed to represent all possible stereoisomers of the compound. It should be understood that the term "compound" includes any or all of such forms, whether explicitly stated or not (although at times, "salts" are explicitly stated).

"Treat", "treating", and "treatment", etc., as used herein, refer to any action providing a benefit to a subject afflicted with a condition or disease such as leukemia, including improvement in the condition through lessening or suppression of at least one symptom, delay in progression of the disease, etc.

Prevention, as used herein, refers to any action providing a benefit to a subject at risk of being afflicted with a condition or disease such as leukemia, including avoidance of the development of cancer or a decrease of one or more symptoms of the disease should leukemia develop. The subject may be at risk due to exposure to a carcinogen, or as a result of family history.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

The methods described herein include administering a therapeutically effective amount of a composition including a compound of Formula I:

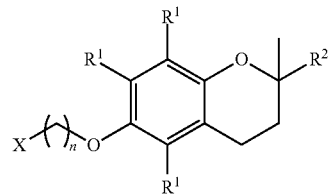

wherein $R^1$ is independently selected from hydrogen and methyl; $R^2$ is selected from the group consisting of 4,8-dimethyl-non-1-enyl, 4,8-dimethyl-nonyl, non-1-enyl, and nonanyl groups; X is a carboxyl, phosphonic, or sulfonic moiety; and n is an integer from 1 to 6, or a pharmaceutically acceptable salt thereof.

Embodiments can include all possible species encompassed by formula I. For example, in additional embodiments of the method, X of the compound of formula I can specifically be a carboxyl moiety, a phosphonic moiety, or a sulfonic moiety.

In further embodiments of the method, $R^2$ of the compound of formula I can specifically be a 4,8-dimethyl-non-1-enyl group, a 4,8-dimethyl-nonyl group, a non-1-enyl group, or a nonanyl group.

In another aspect, the methods described herein include administering a therapeutically effective amount of a composition including a compound of Formula II:

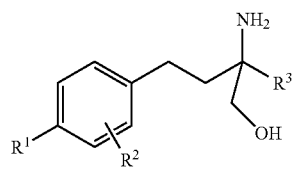

wherein $R^1$ is a $C_6$-$C_{12}$ alkyl or $C_6$-$C_{12}$ alkoxy group; $R^2$ is independently selected from the group consisting of hydrogen, methoxy, and hydroxyl; and $R^3$ is an alkyl or cycloalkyl group; or a pharmaceutically acceptable salt thereof.

Embodiments can include all possible species encompassed by formula II. For example, in some embodiments, $R^1$ of the compound of formula II can be $C_6$-$C_{12}$ alkyl, while in other embodiments $R^1$ of the compound of formula II can be $C_6$-$C_{12}$ alkoxy. In further embodiments, $R^1$ of the compound of formula II can be $C_8$ alkyl or $C_8$ alkoxy.

In additional embodiments, other groups may be varied. For example, in some embodiments, $R^2$ of the compound of formula II is hydrogen. In further embodiments, $R^3$ of the compound of formula II is selected from the group consisting of propyl, isopropyl, isobutyl, cyclopropyl methyl, and cyclobutyl methyl.

In yet further embodiments, specific compounds may be used. For example, in some embodiments, the compound of formula II is FTY720-OMe or FTY20, which have the following structures:

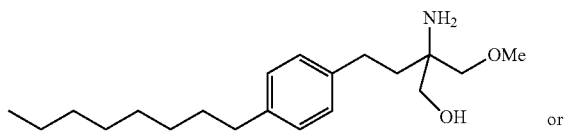

or

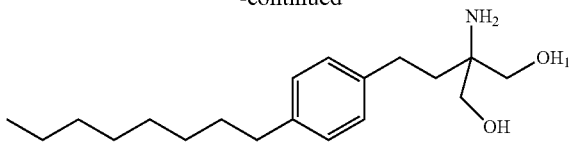

In other embodiments, the compound of formula II is OSU-2S, which has the following structure:

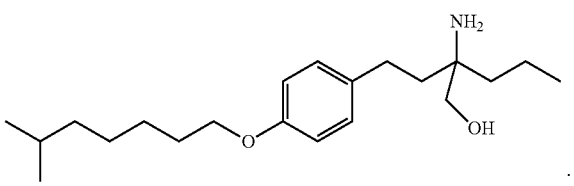 [SMILES: CCCC(N)(CO)CCc1ccc(OCCCCCC(C)C)cc1]

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Treatment of Leukemia Using PP2A Activating Agents

The present invention provides a method of inhibiting the growth of leukemic hematopoietic stem cells in a subject with leukemia by administering to the subject a pharmaceutical composition including a compound of formula I or formula II or a pharmaceutically acceptable salt thereof.

Leukemia is a type of cancer of the blood or bone marrow characterized by an abnormal increase of immature white blood cells. Leukemia includes both acute and chronic leukemia. Acute leukemia is characterized by a rapid increase in the numbers of immature blood cells. Crowding due to such cells makes the bone marrow unable to produce healthy blood cells. Immediate treatment is required in acute leukemia due to the rapid progression and accumulation of the malignant cells, which then spill over into the bloodstream and spread to other organs of the body. Chronic leukemia, on the other hand, is characterized by the excessive build up of relatively mature, but still abnormal, white blood cells. Typically taking months or years to progress, the cells are produced at a much higher rate than normal, resulting in many abnormal white blood cells. Whereas acute leukemia must be treated immediately, chronic forms are sometimes monitored for some time before treatment to ensure maximum effectiveness of therapy.

Additionally, the diseases are subdivided according to which kind of blood cell is affected. This split divides leukemias into lymphoblastic or lymphocytic leukemias and myeloid or myelogenous leukemias. In lymphoblastic or lymphocytic leukemias, the cancerous change takes place in a type of marrow cell that normally goes on to form lymphocytes, which are infection-fighting immune system cells. Most lymphocytic leukemias affect the B cell lymphocytes. In myeloid or myelogenous leukemias, the cancerous change takes place in a type of marrow cell that normally goes on to form red blood cells, various other types of white cells, and platelets.

Combining these two classifications provides the majority of known types of leukemia, though other more rare types of leukemia are also know. Acute lymphoblastic leukemia (ALL) is the most common type of leukemia in young children. Subtypes include precursor B acute lymphoblastic leukemia, precursor T acute lymphoblastic leukemia, Burkitt's leukemia, and acute biphenotypic leukemia. Chronic lymphocytic leukemia (CLL) most often affects adults over the age of 55. One subtype is B-cell prolymphocytic leukemia, a more aggressive disease. Acute myelogenous leukemia (AML) occurs more commonly in adults than in children, and more commonly in men than women. Subtypes of AML include acute promyelocytic leukemia, acute myeloblastic leukemia, and acute megakaryoblastic leukemia. Chronic myelogenous (i.e., myeloid) leukemia (CML) occurs mainly in adults. One subtype is chronic monocytic leukemia. Additional types of leukemia include Hairy cell leukemia (HCL), T-cell prolymphocytic leukemia (T-PLL), Large granular lymphocytic leukemia, and Adult T-cell leukemia, which is caused by human T-lymphotropic virus (HTLV).

Various symptoms are associated with leukemia, depending on the type of cells affected. Damage to the bone marrow can result in a lack of blood platelets causing subjects with leukemia to often become easily bruised, bleed excessively, or develop pinprick bleeds (petechiae). Lack of white blood cells can cause the patient's immunosuppression, which in some cases results in frequent infection, ranging from infected tonsils, sores in the mouth, or diarrhea to life-threatening pneumonia or opportunistic infections. A red blood cell deficiency, on the other hand, leads to anemia, which may cause dyspnea and pallor. Other symptoms such as fever, chills, night sweats, fatigue, nausea, and weight loss can also occur.

Of particular interest for the present invention are leukemias that include the Philadelphia (Ph) chromosome. The Ph chromosome is formed by a balanced translocation between chromosomes 9 and 22, i.e., t(9;22)(q34;q11.2). The critical genes involved in the translocation are ABL1, from 9q34, which is translocated into a specific gene, BCR, on chromosome 22. The Philadelphia chromosome is known to be present in forms of both chronic myelogenous leukemia and acute lymphoblastic leukemia.

Chronic myelogenous leukemia, BCR-ABL1+ (CML) is a myeloproliferative neoplasm that originates in a pluripotent bone marrow stem cell and is consistently associated with the BCR-ABL1 fusion gene. This genetic abnormality results from translocation of ABL1 on chromosome 9 to the region of the BCR gene on chromosome 22. The resulting fusion gene encodes an abnormal protein with constitutively activated tyrosine kinase activity that is responsible for the activation of signal transduction pathways that lead to the abnormal bone marrow proliferation and to the clinical and morphologic manifestations of this unique leukemia.

Approximately one-fourth of adult acute lymphoblastic leukemia (ALL) expresses the oncogenic protein BCR-ABL1 that results from the t (9;22) chromosome translocation known as the Philadelphia (Ph) chromosome. Ph-positive (Ph+) ALL is associated with at least a 10% lower chance of complete remission (CR) than Ph-negative (Ph−) disease and with an extremely poor prognosis overall, with a median survival of 8 months Hematopoietic stem cells (HSCs) are multipotent stein cells that give rise to all the blood cell types from the myeloid. These blood cell types include monocytes and macrophages, neutrophils, basophils, eosinophils, erythrocytes, megakaryocytes/platelets, dendritic cells, and lymphoid lineages (T-cells, B-cells, NK-cells). hematopoietic tissue contains cells with long-term and short-term regeneration capacities and committed multipotent, oligopotent, and unipotent progenitors. HSC are defined by their ability to replenish numerous blood cell types (multipotency) and their ability to self-renew.

Hematopoietic stein cells generally resemble lymphocytes. However, hematopoeitic stem cells can be identified by their small size, lack of lineage markers, low staining with vital dyes such as rhodamine 123 or Hoechst 33342, and presence of various antigenic markers on their surface such as CD34+, CD59+, Thyl/CD90+, CD38lo/−, C-kit/CD117+, and lin−. In leukemic patients, cancerous hematopoietic stem cells can be difficult to eliminate, and failure to inhibit the growth of these cells can result in resurgence of the leukemia after treatment. Accordingly, in one aspect of the invention, a method of inhibiting the growth of leukemic hematopoietic stem cells in a subject with leukemia is described that includes administering a therapeutically effective amount of a composition including a compound of formula I or II. The pharmaceutical composition can also include any of the more specific embodiments of the compounds of formula I or II described herein.

The compounds of the invention can be used to provide prophylactic and/or therapeutic treatment of a subject. The compounds of the invention can, for example, be administered prophylactically to a subject in advance of the occurrence of leukemia. Prophylactic (i.e., preventive) administration is effective to decrease the likelihood of the subsequent occurrence of leukemia in the subject, or decrease the severity of cancer that subsequently occurs. Prophylactic treatment may be provided to a subject that is at elevated risk of developing leukemia, such as a subject with a family history of leukemia or exposure to high levels of carcinogens.

Alternatively, the compounds of the invention can, for example, be administered therapeutically to a subject that is already afflicted by leukemia. In one embodiment of therapeutic administration, administration of the compounds is effective to eliminate the leukemia; in another embodiment, administration of the compounds is effective to decrease the symptoms of the leukemia or lengthen the lifespan of the subject so afflicted.

The subject can be any animal. However, the subject is preferably a mammal, such as a domesticated farm animal (e.g., cow, horse, pig) or pet (e.g., dog, cat). More preferably, the subject is a human.

The methods of treatment using PP2A activating compounds can have differing effects on leukemic hematopoietic stem cells depending on a variety of factors. In some embodiments, the compounds inhibit the growth of the leukemic hematopoietic stem cells. Inhibiting the growth of the leukemic hematopoietic stem cells indicates that the growth of the stem cells has been decreased from what would have been seen in the absence of the PP2A activating compound. For example, the PP2A activating agent can decrease the growth of the leukemic stem cells by about 10%, 20%, 30%, 40%, 50%, 60%, 70%, 80%, 90%, or 100%. Growth inhibition can also be referred to as a cytostatic effect. In other embodiments, the composition has a cytotoxic effect on leukemic hematopoietic stem cells. A cytotoxic effect refers to killing all or a portion of the leukemic hematopoietic stem cells. For example, a cytotoxic effect can kill up to about 10%, 20%, 30%, 40%, 50%, 60%, 70%, 80%, 90%, or 100%. In some embodiments, both cytostatic and cytotoxic effects are seen.

In additional embodiments, the PP2A activating compounds can be used together with other forms of cancer treatment. For example, the PP2A activating compounds can be co-administered with another anticancer agent. The administration can be simultaneous or asynchronous. The administration of another anticancer agent can provide an additive effect, or preferably a synergistic effect. For example, the administration of the PP2A activating compound can render leukemic hematopoietic stem cells more sensitive to the effect of another anticancer compound. Examples of anticancer compounds include alkylating agents, anti-metabolites, plant alkaloids and terpenoids, topoisomerase inhibitors, and cytotoxic antibiotics. Specific anticancer agents within these classes, as well as anticancer agents that fall outside of these classes, are well-known to those skilled in the art.

Administration and Formulation of the Compounds of the Invention

The present invention also provides pharmaceutical compositions that include compounds such as those defined by formula I or formula II as an active ingredient, and a pharmaceutically acceptable liquid or solid carrier or carriers, in combination with the active ingredient. Any of the compounds described above as being suitable for the treatment of cancer can be included in pharmaceutical compositions of the invention.

The compounds can be administered as pharmaceutically acceptable salts. Pharmaceutically acceptable salt refers to the relatively non-toxic, inorganic and organic acid addition salts of the compounds. These salts can be prepared in situ during the final isolation and purification of the compounds of the invention, or by separately reacting a purified compound of the invention with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions include one or more compounds of the invention together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated compounds can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the active compound, or as a solution or suspension in an aqueous liquor or non-aqueous liquid such as a syrup, an elixir, an emulsion, or a draught. Such compositions and preparations typically contain at least about 0.1 wt-% of the active agent. The amount of the compound of the invention (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts. See for example the discussion of the preparation of PP2A in US Patent Publication 2010/0267673 and FTY720-derived compounds in U.S. patent application Ser. No. 13/305,927, the disclosures of which are incorporated herein by reference. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, N.Y., (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

The present invention is illustrated by the following example. It is to be understood that the particular examples, materials, amounts, and procedures are to be interpreted broadly in accordance with the scope and spirit of the invention as set forth herein.

EXAMPLE

Background: The success of tyrosine kinase inhibitors (TKIs) depends on the addiction of Philadelphia-positive (Ph$^+$) CML progenitors to BCR-ABL1 kinase activity. However, CML quiescent hematopoietic stem cells (HSC) are TKI-resistant and represent an active disease reservoir. We hypothesize that Ph$^+$ stemness requires inhibition of the tumor suppressor protein phosphatase 2A (PP2A). PP2A is reactivated by FTY720, a drug that targets CML but not normal progenitors. Here we investigated the mechanism controlling survival/self-renewal of quiescent leukemic HSCs and their sensitivity to PP2A-activating drugs.

Methods

Cell lines. The 32Dcl3 and K562 cell lines were maintained in culture in Iscove's modified Dulbecco's medium (IMDM)/10% FBS/2 mM L-glutamine. The 32D-p210$^{BCR\text{-}ABL1}$, the p210$^{K3172R}$ and the JAK2-expressing 32Dcl3 cells were generated by retroviral infection as previously described. Perrotti et al., Nat Genet 30, 48-58 (2002).

Primary Cells. Progenitors (CD34$^+$) and HSC-enriched fractions (CD34$^+$/CD38$^-$; CD34$^+$/CD38$^-$/CD90$^+$) were isolated from umbilical cord blood (UCB) and from mononuclear cells from bone marrow (BM) or peripheral blood (PB) of unidentifiable chronic (CP, n=34), accelerated (AP, n=6) and blastic (BC, n=56) phase CML (n$_{TOT}$=96) and healthy (n=27) donors. Frozen samples of CD34$^+$ normal BM (NBM) cells from different healthy donors were obtained from Cincinnati Children's Hospital and OSU. All studies were performed with human CML specimens obtained from The Ohio State University Leukemia Tissue Bank; the Division of Hematology, Maisonneuve-Rosemont Hospital, Montréal QC, from the North Glasgow University Hospital Division, University of Glasgow UK, from the Hammersmith Hospital, Imperial College, London UK, and from the Department of Hematology, Aarhus University Hospital, Denmark, and were carried out with approval from The Ohio State University Institutional Review Board. The percentage of CML (CP and BC) Ph+ cells analyzed by FISH ranged from 75% to 100%. Umbilical cord blood (UCB) units were collected by the Translational Trials Development Support Laboratory of Cincinnati Children's Hospital Research Foundation according to an IRB approved protocol.

Mouse marrow cells were obtained from the femurs and tibias of wild-type FVB/N mice and from 8-week induced leukemic SCLtTA/BCR-ABL1 mice. Koschmieder et al., Blood 105, 324-334 (2005). Bone marrow mononuclear cells were used for the isolation of the Lin-fraction (lineage depletion kit, Miltenyi Biotech). When cultured, murine stem/progenitor cells were kept in complete IMDM supplemented with murine IL-3 (2 ng/ml), IL-6 (1.2 ng/ml), KL (10 ng/ml), Flt-3 ligand (5 ng/ml) and GM-CSF (5 ng/ml). Cells were treated as indicated with the following reagents: imatinib mesylate (Novartis); 1,9-dideoxyforskolin, JAK inhibitor I (EMD Chemicals); TG101210, TG101348 (TargeGen Inc.), lithium chloride (Fisher), SB216763 (Cayman Chemicals). FTY720 was synthesized with subsequent HPLC purification (Seidel et al., J Org Chem 69, 3950-3952 (2004)), and identity/purity was confirmed by nuclear magnetic resonance and mass spectrometry. (S)-FTY720-OMe, OSU-2S and (S)-FTY720-regioisomer were synthesized as described. Lim et al., Cell Signal 23, 1590-1595 (2011). Omar et al., Hepatology 53, 1943-1958 (2011).

Flow cytontetric analysis and sorting of HSCs. Primary $CD34^+$ cells were isolated by magnetic cell sorting (CD34 MultiSort; Miltenyi Biotec) and kept in IMDM supplemented with 30% FBS, 2 mM Lglutamine, rhIL-3 (20 ng/ml), rhIL-6 (20 ng/ml), rhFlt-3 ligand (100 ng/ml), and rhKL (100 ng/ml) (Stem Cell Technologies). The CD34+ fraction derived from the BM of healthy donors and the PB or BM from CML patients was stained with anti-CD34 FITC or PE, and anti-CD38 PE-Cy7 (BD Biosciences). The Lin– fraction of murine mononuclear cells was stained with anti-Sca-1 PeCy7 (BD Biosciences) and anti-c-kit APC-AlexaFluor750 (eBioscience), The $CD34^+/CD38^-$ or the Lin–/Sca-1+/c-Kit+ (LSK) fractions were sorted by fluorescence-activated cell sorting with a FACS Aria II instrument (BD Biosciences). Where indicated, the $CD34^+$, and the TKI-resistant $CFSE^+/CD34^+$ fractions from normal or CML samples, and the $CD34^+$ fraction from pHIV7-sp1 shBCR-ABL1 transduced CML samples were stained with anti-CD34 PE and anti-CD38 PE-Cy7 (BD Biosciences), fixed and permeabilized with the BD Cytofix/Cytoperm Kit (BD Biosciences) and, stained with either a specific primary antibody or an isotype matched control and a secondary goat F(ab') anti-rabbit conjugated to Alexa Fluor 647 (Invitrogen); intracellular flow data is reported as fold-change of the isotype-subtracted geometric Median of Fluorescence Intensitiy (MFI) of the Alexa Fluor 647 signal. The primary antibodies used were rabbit anti-phospho-c-Ab1 (pY245), rabbit anti-phospho-JAK2 (pY1007/1008) (Cell Signaling Technology), and rabbit anti-SET (Globozyrne).

CFSE-mediated tracking of cell division. Carboxyfluorescein diacetate succinimidyl diester (CFSE)-stained cells (CellTrace CFSE Proliferation Kit: Invitrogen) were cultured in the presence of the indicated drugs (dosed at time zero and at day three), and the cells were harvested after 3 or 6 days in culture, and stained with anti-CD34 PE, Annexin-V V450, and the viability stain 7-AAD (BD Bioscience) to determine the number of viable quiescent cells ($CFSEmax/CD34^+$/7-AAD– cells) and the percentage of quiescent and apoptosis-committed cells ($CFSEmax/CD34_+/Annexin\ V_+/7-AAD\pm$). Cells were sorted into dividing and quiescent populations for Western blot analysis. For assessment of mouse quiescent leukemic HSCs, Lin- cells from 8 week-induced SCLtTA/BCR-ABL1 mice were CFSE-stained and used as described above. Quiescent cells ($CFSE^{max}/CD34^+$) were reported as a fraction of the initial number of $CD34^+$ cells.

Long term culture-initiating cell (LTC-IC) and Colony-forming cell (CFC)/replating assays. $2\times10^6$ mononuclear CML cells were cultured with a 1:1 mixture of irradiated (80 Gy) IL-3/G-CSF-producing M2-10B4 and IL-3/KL-producing SI/SI murine fibroblasts in MyeloCult H5100 (StemCell Technologies) supplemented with hydrocortisone. Drugs were present during the first week of culture. Medium was replaced after 7 days, followed by weekly half-medium changes. After 6 weeks, adherent and floating cells were harvested and $5\times10^4$ cells plated into MethoCult H4435. LTC-IC-derived colonies were scored after 14 days. For CFC/replating, individual 14-day colonies from $10^3$-$10^5$ $CD34_+/CD38_-$ CML or $0.2\times10^3$-$10^3$ leukemic LSK cells plated in 0.9% H4435 or M3234 MethoCult, respectively, containing KL, G-CSF, GM-CSF, IL-3, IL-6, and Epo were replated and scored 2 weeks later.

LEF/TCF reporter assay. $CD34_+/CD38_-$ CML cells were transduced with pBAR or pfuBAR (negative control) ®-catenin lentiviral reporter constructs (54), puromycin-selected and treated with the indicated drugs. Luciferase was measured using the Bright-Glo Luciferase system (Promega).

Immunofluorescence and proximity ligation assay. $CD34^+/CD38^-$ cells from CML patient samples or LSK cells derived from induced leukemic mice were sorted, treated in liquid culture with the indicated drugs and cytospun onto glass slides. Slides were fixed in 3.7% formaldehyde, pennneabilized with 0.05% Triton X-100, and stained with an Anti-®-catenin primary antibody (Cell signaling), a secondary goat F(ab') anti-rabbit conjugated to Alexa Fluor 647, and the nuclear stain DAPI (Invitrogen); slides were mounted with Slowfade antifade reagent (Invitrogen). Microphotographs were obtained with a Zeiss LSM 510 confocal laser-scanning microscope with C-Apochromat 63/1.2 W objective. A minimum of three fields for each slide were acquired. For the Proximity Ligation Assay (PLA) $CD34_+/CD38_-$ CML cells were treated, fixed, and permeabilized as described above. The slides were then simultaneously stained with a mix of mouse anti-PP2A (Millipore) and rabbit anti-SET (Globozyme) antibodies. The PLA procedure (Duolink; Olink Bioscience) was performed according to manufacturer instructions. An average of 20 z-stack (10 μm sections) were captured with a Zeiss LSM 510 confocal laser-scanning microscope with C-Apochromat 63/1.2 W objective; at least three fields/slide were acquired. Three-dimensional projections were generated and positive signals/cell were calculated by ImageJ software (NIH).

Lentiviral transduction. Lentiviral pseudotyped particles were produced by transient calcium phosphate transfection (ProFection mammalian transfection System, Promega) of 293T cells with the specific lentiviral vector (18 μg/175 cm$^2$), the psPAX2 packaging construct (Addgene plasmid 12260, provided by Dr. D. Trono, Swiss Institute of Technology, Lausanne, Switzerland; 9 μg/175 cm$^2$) and the G-glycoprotein of vesicular stomatitis virus (VSV-G, 1.8 μg/175 cm$^2$). The viral supernatant was collected at 24 h and 48 h post-transfection, mixed 1:4 with a 40% PEG-8000 solution, incubated overnight at 4 C, and concentrated to $\frac{1}{100}^{th}$ of the original volume by centrifugation (30 min, 1500 g at 4° C.). The viral titer was determined by transduction of 293T cells with serial dilutions of concentrated vector, and the percentage of GFP+ cells was determined 48 h after transduction. Target cells ($0.5\times10^6$/ml) were transduced by spinoculation (O'Doherty et al., J Virol 74:10074-10080 (2000). (1200 g for 2 h) with viral supernatants diluted (MOI=10) in polybrene-containing (4 mg/ml) complete medium. GFP-mediated FACS-sorting or puromycin selection was initiated 48 h post-infection.

Plasmids. pHIV7-GFP-sp1: The lentiviral pHIV7-GFP vector containing the shRNA specific for the b3a2 (e14a2)

translocation break-point of BCR/ABL was provided by Dr. John Rossi, Beckman Research Institute, City of Hope, Duarte, Calif., USA. Prior to transduction the presence of the b3a2 BCR-ABL1 translocation was assessed by RT-PCR as previously described. Sidorova et al., Mol Pathol 50, 266-268 (1997). pBAR and pfuBAR: the ®-catenin-responsive luciferase reporter lentiviral vector pBAR contains 12 TCF binding sites separated by 5 nucleotide linkers directly upstream of a minimal TK promoter that drives the expression of firefly luciferase. The pfuBAR reporter is characterized by the substitution of two nucleotides in each TCF elements that makes it unresponsive to ®-catenin. pSRα-p210 and pSRα-p210-K1172R: the plasmid pSR (MSVtkneo-p210 has been described previously. Skorski et al., Embo J 16:6151-6161 (1997). The p210 kinase-deficient (K1172R) mutant was obtained from Dr. Sawyers C. (UCLA, Los Angeles, Calif.). MigR1-p210- (kind gift of Dr. Pear W. S., UPENN, Philadelphia Pa.) and MigR1-p210-K1172R BCRABL have been previously generated by subcloning the wild type and mutated BCR-ABL1 cDNA into the MigR1 EcoR1 site. pNALDINI-HA-PP2Ac: the HA-tagged PP2Ac cDNA was PCR amplified from pHM6-HA-PP2Ac(15) and subcloned into the pNALDINI.CMV.IRES.EGFP lentiviral vector. pGIPZshJAK2: the construct carrying the shRNA targeting human JAK2 was from Open Biosystems (Clone ID: V2LHS_61653).

Western blot analysis and immunoprecipitation. Lysates obtained from cell lines were subjected to SDS-PAGE and western blot. Primary CML cells sorted from the CFSE tracking experiment were lysed in Laemmli buffer (10 $\mu$1/3000 cells), denatured and subjected to SDS-PAGE and Western blot. For immunoprecipitation, cells were lysed in 20 mM HEPES (pH 7.0), 150 mM NaCl, and 0.1% NP-40 supplemented with protease and phosphatase inhibitors. Lysates were precleared for 1.5 h at 4° C., and immunoprecipitated overnight at 4° C. with protein G-plus agarose beads (Calbiochem) coated with anti-SET or anti-Ab1 antibody, and subjected to (Millipore) and immunoblotting. The antibodies used were: anti-Ab1 (Ab-3), anti-actin (EMD); antiphosphotyrosine (4G10), anti-PP2Ac (Millipore); anti-GRB2 (BD Biosciences); anti-®-catenin, antiphospho-®-catenin (pS552), and anti-Jak2 (Cell Signaling Technology); antiphospho-Jak2 (pY1007/1008) (Epitomics); and anti-SET (I2PP2A, Globozyme).

PP2A phosphatase assay. PP2Ac assays from whole cell lysates were carried out using the PP2Ac immunoprecipitation phosphatase assay kit (Millipore). Briefly, protein lysates (50 µg) in 100 µl of 20 mM Hepes. pH 7.0, 100 mM NaCl, 5 µg of PP2Ac antibody (Millipore), and 25 µl of Protein A-agarose were added to 400 µl of 50 mM Tris, pH 7.0, 100 mM $CaCl_2$, and IPs were carried out at 4° C. for 2 h. IPs were used in the phosphatase reaction according to the manufacturer's protocol.

BM Serial Transplantation Assays and In Vivo Effect of FTY720 on LT-HSCs from Transgenic BCR-ABL1 Mice. $2\times10^6$ $GFP_+$ BM or $3\times10^3$ $GFP_+$ BM-derived LSK ($Lin^-/Sca-1^+/Kit^+$) cells from 4-week induced leukemic SCLtTA/BCR-ABL1/GFP mice were transplanted into lethally-irradiated FVB/N mice. After the onset of neutrophilia (4 weeks post-transplant), mice were FTY720- (10 mg/kg/day, i.p.) or vehicle-treated for 4 weeks. The number of total $GFP_+$ cells and $GFP_+$ long-term (LT)-HSCs ($Lin^-/Sca-1^+/Kit^+/FLt3^-/CD150^+/CD48^-$) was measured with a LSRII flow cytometer. BM cells ($2\times10^6$, $1\times10^6$ and $0.5\times10^6$) from treated and untreated animals (8 mice/group) mixed with $2\times10^5$ FVB/N BM cells were transplanted into lethally-irradiated secondary recipients. Engraftment ($GFP^+$ in PB>0.1%) was monitored every 4 weeks, and LT-HSC frequency was determined 16 weeks after secondary transplant using Poisson statistics. All animal studies were IACUC approved.

Engraftment of Human Normal and CML Cells in Immnunodeficient NSG Mice and Effect of FTY720 on Leukemic and Normal Hematopoietic Stem/Progenitor Cells. $CD34_+$ cells were isolated from BM of CML patients (n=3) or from umbilical cord blood specimens (UCB; n=3). Note that CML samples were from patients in blastic transformation with ≥75% of Ph+ blasts. Sublethally irradiated (260 rads) 6-8 week-old NOD.Cg-Prkds$^{scid}$ IL2rg$^{tm1Wjl}$/SzJ (NSG, Jackson Laboratory) mice were intrafemorally injected with $1-3\times10^6$ CML or $10^5$ UCB $CD34^+$ cells/mouse. The engraftment was assessed 8 weeks post-transplant by anti-human CD45 (BD Biosciences) and anti-mouse CD45.1 flow staining of intrafemoral BM aspirates and PB from tail vein. Wunderlich et al., Leukemia 24, 1785-1788 (2010). CML- and UCB-engrafted NSG mice were treated for 8 weeks (8-10 mice/group) with either FTY720 (10 mg/kg/day; i.p.) or PBS. Disease evolution and effect of FTY720 on HSC-enriched cell fraction ($CD45^+/CD34^+/CD38^-$), primitive progenitors (CD45+/CD34+), myeloid ($CD45^+/CD34^+/CD33^+$), B-cell ($CD45^+/CD19^+$) and T-cell ($CD45^+/CD3^+$) compartments were determined before and after 4/8 weeks of FTY720 treatment by FACS-mediated analysis of BM aspirates and/or PB cells. BCR-ABL1 transcript levels were monitored by qRT-PCR-mediated (Ipsogen) analysis of BCR-ABL1/human Abl1 ratios in total RNA samples derived from BM-aspirates of CML-engrafted animals at time of engraftment (time 0) and after 8 weeks of FTY720 treatment. Notably, adverse effects or changes in animal behavior have not been noted in FTY720-treated animals. These studies were performed by IRB and IACUC approved protocols.

Fluorescent in situ hybridization (FISH). Human $CD45_+$ cells from intrafemoral BM aspirates of untreated and 8 weeks FTY720-treated NSG mice engrafted with $CD34_+$ CML-BC and UCB cells, were FACS-isolated, dropped onto microscope slides, and fixed in a solution of three parts methanol and one part acetic acid. A triple color, dual fusion BCR/ABL1 FISH probe was applied according to the manufacturer's instructions (Kreatech Diagnostics). Hybridized slides were counterstained with DAPI and visualized under an Olympus BX41 microscope. Images were captured using a Hammamatsu Orca II CCD camera and SmartCapture X software (Digital Scientific).

Statistical analysis. Student t-tests were performed using GraphPad-Prism v5.0a. The p-values are indicated as: *<0.05, <0.01 and *<0.001.

Results

Survival and self-renewal of TKI-resistant quiescent $pH^+$ HSCs requires PP2A silencing and is modulated by FTY720. In the stem cell-enriched CD34+/CD38− cell fraction levels of PP2A phosphatase activity were ~77% and 84% lower in CML chronic phase (CML-CP, n=3) and blast crisis (CML-BC, n=3), respectively, than in HSC derived from the bone marrow of healthy (NBM, n=4) individuals (FIG. 1). Furthermore, treatment of leukemic, HSCs with FTY720, used at a non-toxic concentration for normal CD34+ progenitors, restored PP2A activity at levels superimposable to those observed in the identical cell fraction from healthy donors (light grey bar). As expected, PP2A activity was inhibited in CD34+/CD38+ CML-CP compared to normal progenitors (dotted bars) and in BCR-ABL1-expressing compared to vector-expressing myeloid 32Dcl3 precursors (lined bars). Accordingly, levels of the endogenous PP2A inhibitor SET/

Figure 2:
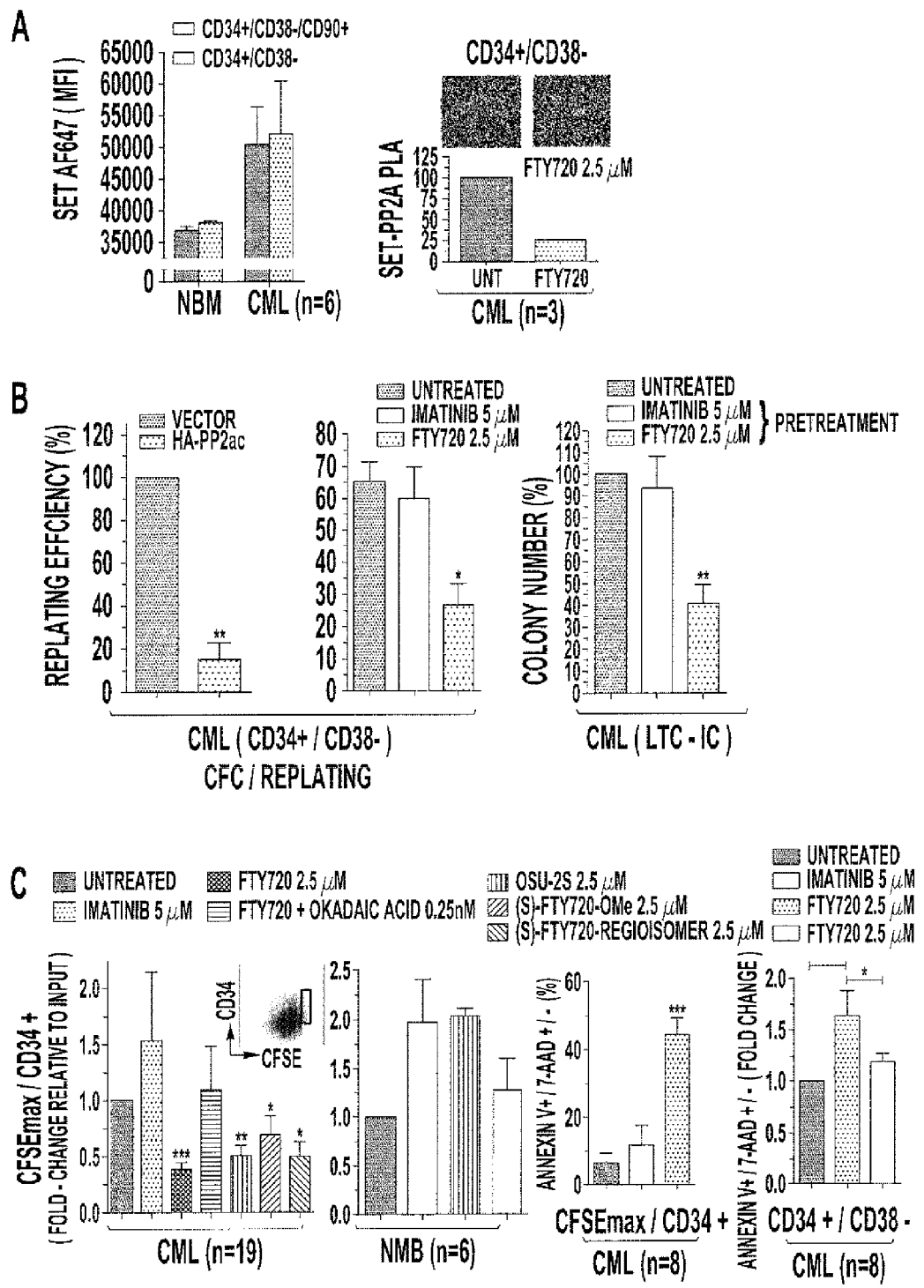
FIG. 2 provides bar graphs showing that FTY720 decreases survival and self-renewal of quiescent Ph$^+$ HSCs. (A): (left): SET protein levels measured by intracellular flow-staining and expressed as geometric Mean of Fluorescence Intensity (MFI), in CD34$^+$/CD38$^-$ and CD34$^+$/CD38$^-$/CD90$^+$ fractions from Bone Marrow (BM) of healthy (Normal Bone Marrow; NBM) and chronic myeloid leukemia (CML) donors. (right): Confocal microphotographs show SET-PP2A association by quantitative (graph) proximity ligation assays (PLA; n=3) on untreated and FTY720-treated (24 h) CD34$^+$/CD38$^-$ CML cells. (B): CFC/Replating: replating efficiency of single CFC colonies from CD34$^+$/CD38$^-$ CML cells ectopically expressing HA-PP2Ac (left) or treated with FTY720 or imatinib (right); Student's t-test. LTC-IC: number of colonies derived from clonogenic assays of CML cells cultured for six weeks and exposed to the indicated drug during the first week of culture. (C): First two graphs: number of quiescent CFSE$^{max}$/CD34$^+$ cells (gated cells; inset) in untreated and drug-treated CFSE-labeled CD34$^+$ NBM and CML BM cells. Third and fourth graphs: Annexin-V/7-AAD staining shows percentage of CFSE$^{max}$/CD34$^+$ or CD34$^+$/CD38$^-$ CML cells undergoing apoptosis. Student's t-test.

I2PP2A (SET) were significantly higher in CML than NBM CD34+/CD38− and CD34+/CD38−/CD90+ (FIG. 2A).

The relevance of PP2A silencing in Ph+ HSC self-renewal and growth/survival was assessed by CFC/replating and LTC-IC assays. A significant 70-90% reduction in replating efficiency was observed upon HA-PP2Ac lentiviral-transduction (P<0.01) (n=3) or FTY720 treatment (P<0.01) of CD34+/CD38−CML (n=3) and LSK (n=6) SCLtTA/BCR-ABL1 (FIG. 2B) cells. Similarly, LTC-ICs were inhibited by 60-70% (P<0.01) in FTY720-pretreated (n=9) compared with untreated (n=9) CML cells (FIG. 1B). As expected, imatinib did not alter CFC/replating and LTC-IC efficiency of CML (n=6) and SCLtTA/BCR-ABL1 (n=3) HSCs (FIG. 2B).

To determine whether FTY720 inhibits self-renewal/survival by reducing the number of TKI-resistant Ph+ HSCs, changes in the proportion of quiescent ($CFSE^{max}$) HSCs (FIG. 2C) were determined in CFSE-labeled CD34+ CML (n=19) and Lin− SCLtTA-BCR-ABL1 (n=4) cells exposed to 2.5 µM FTY720. To assess apoptosis, CFSE+ CML cells (n=12) were Annexin-V labeled. FTY720 triggered apoptosis (FIG. 2C) and induced a 60-75% (P<0.001) and 70-90% decrease in CML (FIG. 2C) and SCLtTA/BCRABL1 $CFSE^{max}$ HSCs, respectively. This effect was PP2A-mediated as it was antagonized by 0.25 nM okadaic acid, which inhibits PP2A activity only (FIG. 2C). Consistent with the lack of FTY720 activity on normal CD34+ BM progenitors, the frequency of quiescent HSCs from NBM (n=6) was not influenced by FTY720 (FIG. 2C).

FTY720 and its non-immunosuppressive derivatives do not harm normal quiescent HSCs. Although more than 90% of intracellular FTY720 remains unphosphorylated in BCR-ABL1+ cells, FTY720 induces lymphopenia upon phosphorylation and S1PR1-mediated internalization. Zemann et al., Blood; 107: 1454-8 (2006). Thus, the activity of three FTY720 derivatives, (S)-FTY720-OMe, (S)-FTY720-regioisomer and OSU-2S that activated PP2A without triggering S1PR1 internalization or inducing B-lymphopenia was tested. These drugs significantly reduced the CML (n=9) but not normal (n=6) $CFSE^{max}$ cells (FIG. 2C). Conversely, the phosphorylated and immunosuppressive FTY-P, which lacks PP2A-activating function, failed to induce apoptosis of CD34+/CD38− CML cells (n=8; P<0.05) (FIG. 2C).

Figure 3:
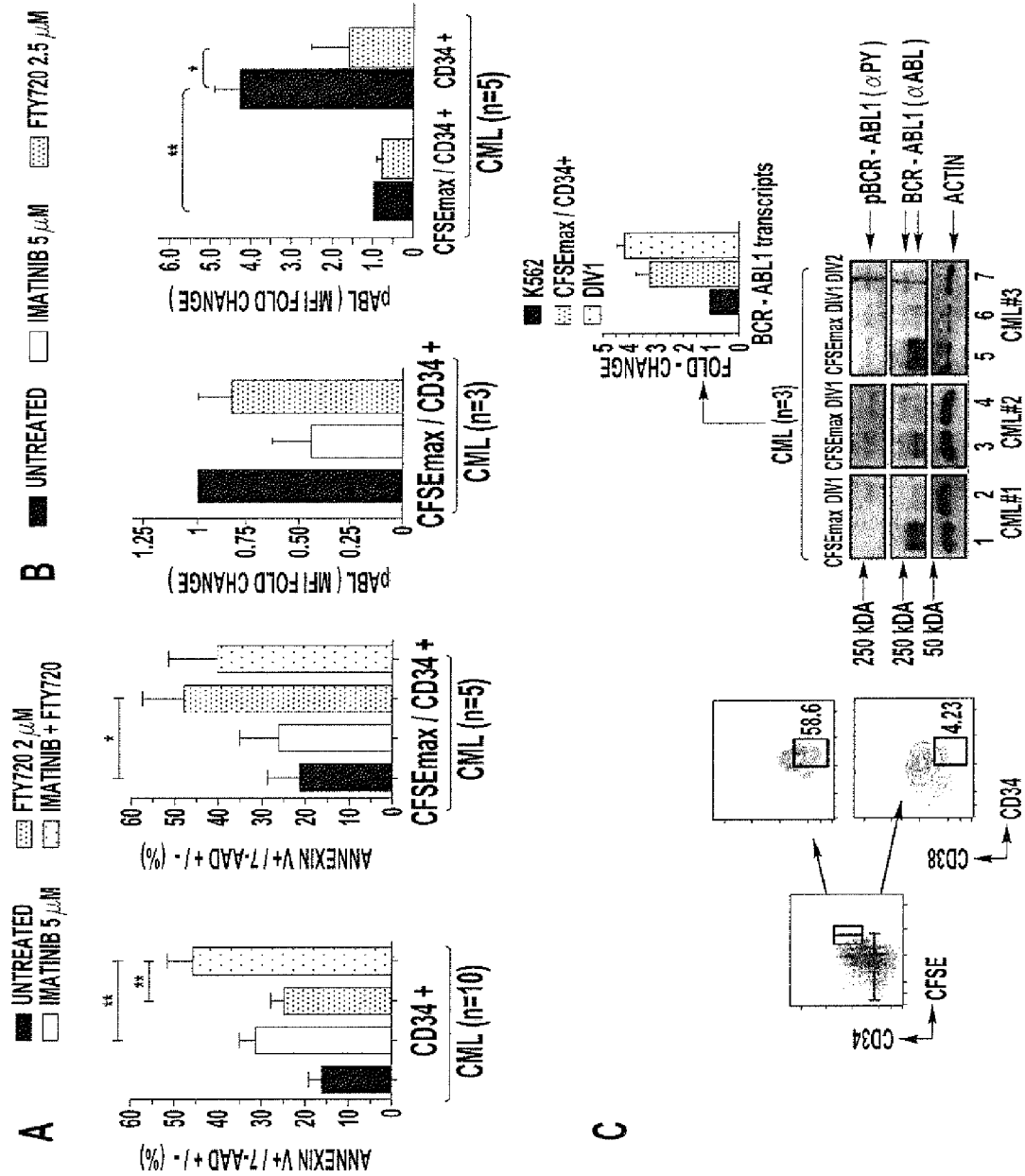
FIG. 3 provides bar graphs and protein blots showing BCR-ABL1 activity, but not its expression, is low in CML quiescent stem cells. (A): Annexin-V/7-AAD staining shows percentage of apoptotic CD34$^+$ CML progenitors and CFSE$^{max}$/CD34$^+$ TKI-resistant quiescent CML cells upon exposure to FTY720 and imatinib used alone or in combination. (B): Levels (expressed as MFI) of active BCR-ABL1 (pABL) in CFSE$^{max}$/CD34$^+$ and CD34$^+$ cells from untreated and FTY720- or imatinib treated CML samples; Student's t-test. (C): (left): Dot plots show gating strategy to isolate quiescent CFSE$^{max}$/CD34$^+$ cells versus dividing CD34$^+$ cells and their CD34-CD38 flow profile; (right): BCR-ABL1 activity (anti-PY), protein (anti-Ab1) and mRNA (inset, relative to Ph$^+$ K562 cells) levels in FACS-sorted quiescent (CFSEmax) compared to dividing (div 1 and div 2) CD34$^+$ CML cells. Actin levels were detected as a control.

BCR-ABL1 kinase activity is dispensable for FTY720-induced apoptosis of quiescent HSCs. FTY720 induces PP2A-dependent BCR-ABL1 dephosphorylation and synergizes with imatinib to trigger apoptosis of CD34+ CML progenitors (n=10) (FIG. 3A). However, FTY720-induced inhibition of BCR-ABL1 activity (pABL levels) occurred in the bulk but not in the quiescent fraction ($CFSE^{max}$) of CD34 CML cells (n=5) (FIG. 3B). In these cells FTY720-induced apoptosis was not influenced by BCR-ABL1 kinase inhibition (n=5) (FIGS. 3A and 3B), as suppression of BCR-ABL1 activity (FIG. 3B) did not result in apoptosis of quiescent CML HSCs (FIG. 1C). Interestingly, 4- to 5-fold lower BCR-ABL1 activity, which did not depend on decreased BCR transcription (inset, FIG. 3C), was found in $CFSE^{max}$/CD34+ compared with CD34+ untreated CML cells (n=5; P<0.01) (FIG. 3B). Analysis of $CFSE^{max}$ and dividing (div1 and div2) HSCs (n=3) showed higher BCR-ABL1 levels (anti-ABL) in quiescent than proliferating cells (FIG. 3C). Enhanced BCR-ABL1 activity did not account for this effect, as levels of phosphorylated BCR-ABL1 (anti-PY) in quiescent HSCs were reduced or identical to those in dividing cells (FIG. 3C). These results along with the evidence that the kinase-deficient K1172R BCR-ABL1 mutant also induced PP2A silencing, suggested that BCR-ABL1 expression alone is critical for CML HSC survival.

Figure 4:
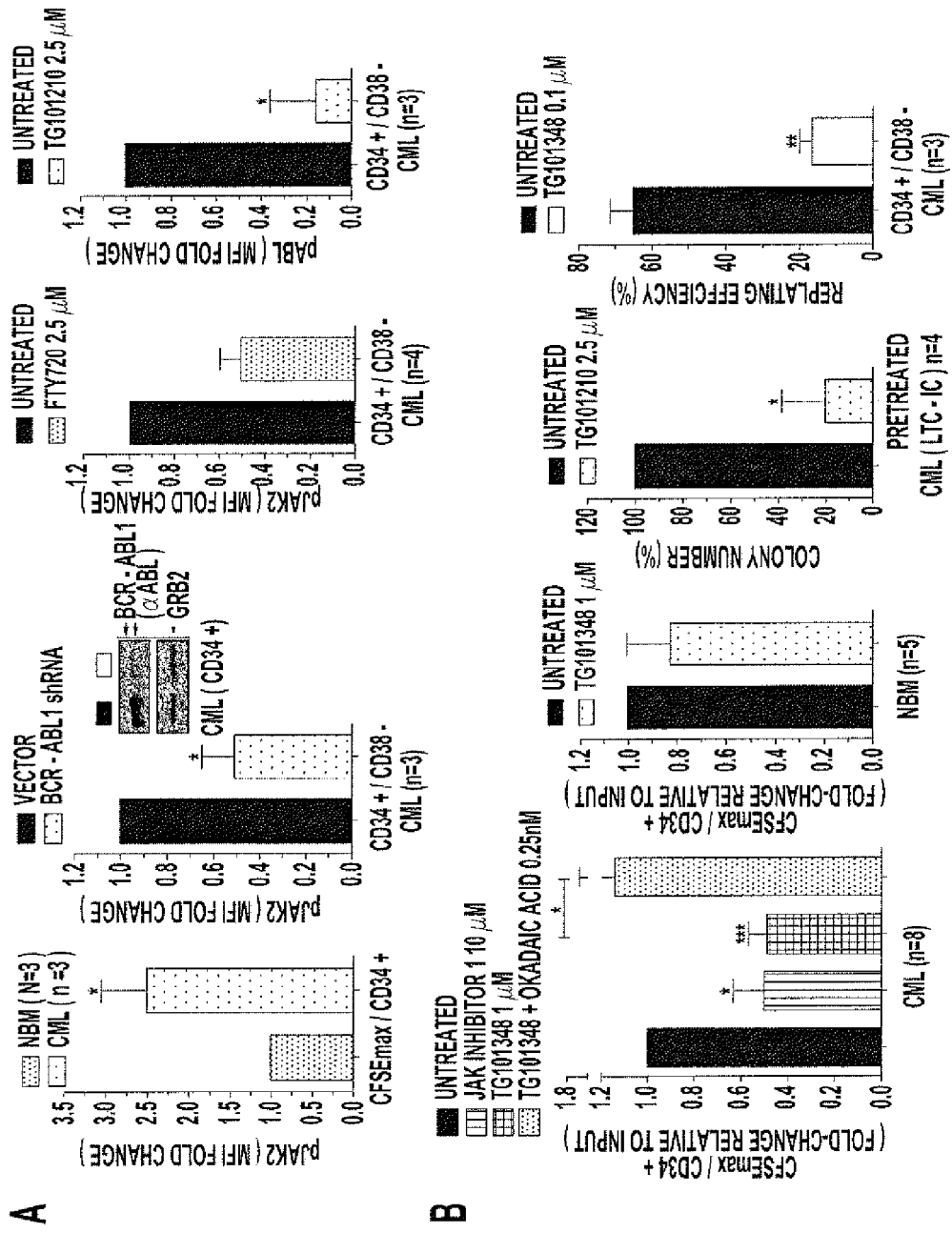
FIG. 4 provides bar graphs showing that JAK2 activity requires BCR-ABL1 expression and is essential for Ph$^+$ HSCs survival. (A): Levels (expressed as MFI) of active JAK2 (pJAK2) and BCR-ABL1 (pABL) in untreated, BCR-ABL1 shRNA-expressing and FTY720-treated CFSE$^{max}$/CD34$^+$ and CD34$^+$/CD38$^-$ cells from NBM and/or CML samples; Student's t-test. inset: BCR-ABL1 levels in CML CD34$^+$ cells transduced with a shRNA specific for the b3a2 BCR-ABL1 junction. (B): (left to right) Effect of Jak2 inhibitors on CFSE$^{max}$/CD34$^+$ frequency, LTC-IC (6 weeks) and replating efficiency of CML cells; Student's t-test.

FTY720 impairs JAK2 activation, which requires BCR-ABL1 expression and is essential for Ph+ HSCs Survival. In BCR-ABL1+ myeloid progenitors, JAK2 interacts with BCR-ABL1 and upregulates SET leading to PP2A inactivation while forced PP2A reactivation results in JAK2 inhibition. Because JAK2 activity is equally induced by wild-type and kinase-deficient BCR-ABL1, and BCRABL1 activity in CD34+/CD38− cells is further reduced by JAK2 inhibition (FIG. 4A), it is possible that JAK2 is recruited by BCR-ABL1 to control HSC survival independently from its kinase activity and through PP2A inhibition. Indeed, JAK2 activity was strongly enhanced in CML (n=3) compared to NBM (n=3) $CFSE^{max}$/CD34+ cells (FIG. 4A), and suppressed upon shRNA-mediated BCR-ABL1 downregulation (n=3) or FTY720 treatment (n=3) (FIG. 4A). Pharmacologic JAK2 inhibition by TG101348 decreased by ~80% and ~75% the CML LTC-IC (n=4) and CFC/replating (n=3) activities, respectively, and by 50% the number of $CFSE^{max}$/CD34+ CML (n=8) but not NBM (n=5) cells, in an okadaic acid-sensitive manner (n=5) (FIG. 4B). This indicated that the effect of JAK2 inhibition on CML HSC survival/self-renewal is mediated by PP2A.

Figure 5:
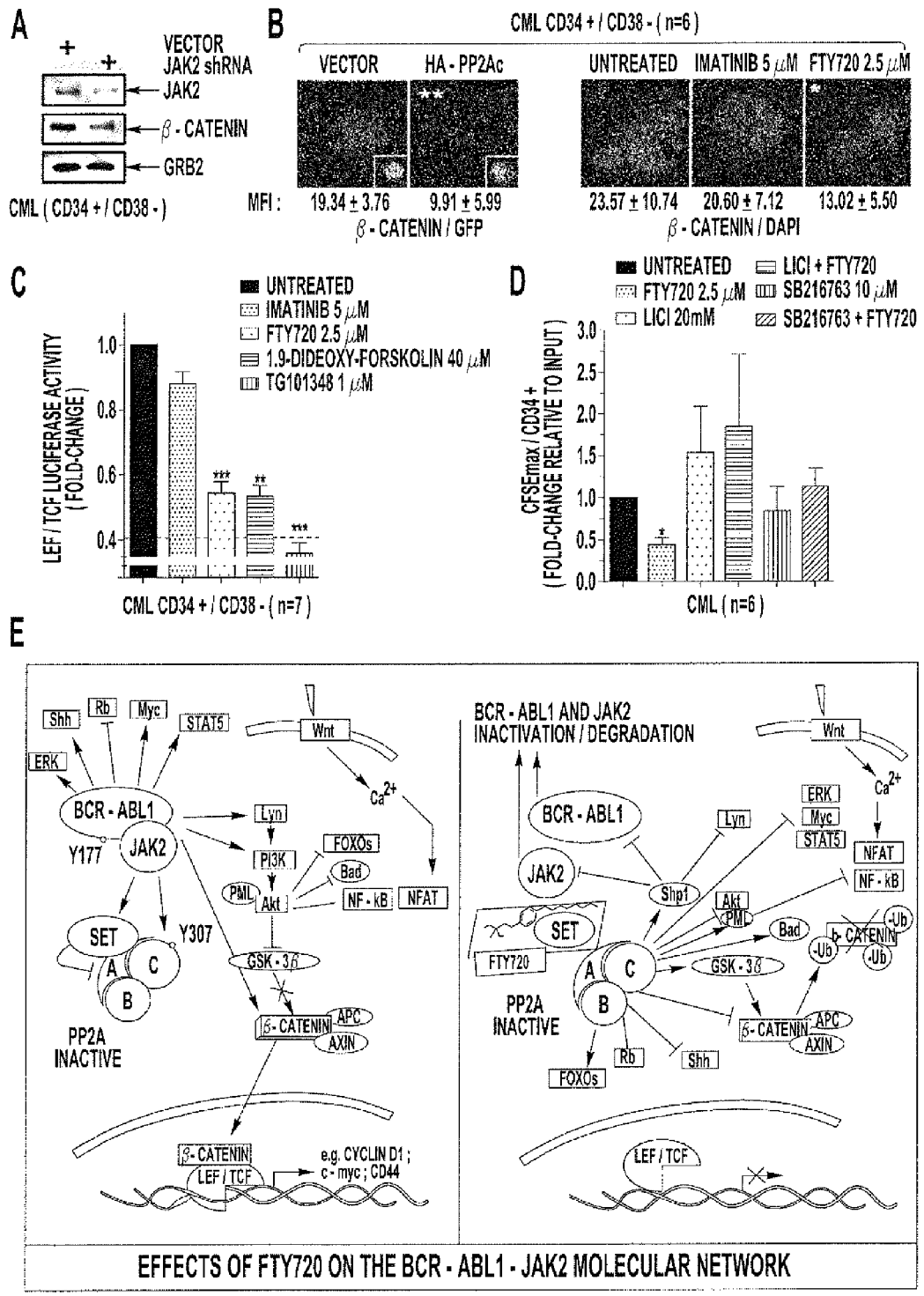
FIG. 5 provides Western blots, microphotographs, bar graphs, and schematic illustrations showing that β-catenin activity is controlled by PP2A and JAK2 in a BCR-ABL1 kinase-independent manner. (A): Western blot shows effect of JAK2 downregulation by shRNA on β-catenin expression in CML CD34$^+$/CD38$^-$ cells. Grb2 was detected as a control, (B): Confocal microphotographs, representative of three independent experiments, show expression levels (MFI±SD) of β-catenin in CML CD34$^+$/CD38$^-$ cells lentivirally-transduced with HA-PP2Ac (left) or treated with FTY720 or imatinib (right). (C): Luciferase assays show β-catenin-driven (LEF/TCF) transcriptional activity in CD34$^+$/CD38$^-$ CML cells untreated or treated with the indicated drugs. The dashed line shows the baseline luciferase levels in cells transduced with the negative control pfuBAR. (D): Effect of GSK3β inhibitors on FTY720-induced reduction of quiescent CFSE$^{max+}$/CD34$^+$ cells. (E): Schematic representation of the BCR-ABL1/Jak2-SET/PP2A-GSK3β/β-catenin molecular network in untreated (left) and FTY720-treated (right) stem and progenitor CML cells.

PP2A and JAK2 control β-catenin activity in a BCR-ABL1 kinase-independent and FTY720-sensitive manner. shRNA-mediated JAK2 downregulation in CD34+/CD38− CML cells significantly decreased the expression of β-catenin (FIG. 5A), a Wnt-signaling factor essential for normal and leukemic stemness (Fleming et al., Cell Stem Cell, 2, 274-83 (2008)) and negatively regulated by PP2A. Seeling et al., Science, 283, 2089-91 (1999). Immunofluorescence revealed that β-catenin expression is markedly decreased in HA-PP2Ac-expressing or FTY720-treated Ph+CD34+/CD38− cells (n=3) (FIG. 5B). Notably, FTY720 (n=3) but not imatinib (n=3) induced β-catenin degradation in CD34+/CD38− CML, leukemic LSK, and 32D-BCR/ABL cells (FIG. 5B), consistent with the notion that PP2A inactivates/downregulates β-catenin. The importance of pharmacologic PP2A activation for β-catenin function, its dependence on JAK2 but not BCR-ABL1 activity was confirmed by LEF/TCF luciferase assays in CD34+/CD38− CML (n=7) and 32D-BCR/ABL cells. In fact, the PP2A activators FTY720 (n=6) or 1,9-dideoxy-forskolin (n=3), the JAK2 inhibitor TG101348 (n=3), but not imatinib (n=4) markedly impaired β-catenin transcriptional activity (FIG. 5C). As β-catenin inactivation depends on phosphorylation by GSK-3β, the role of GSK-3β in FTY720-induced apoptosis of quiescent Ph+ HSCs was assessed. Treatment of CD34+ CML cells (n=6) with the GSK-3β inhibitors LiCl and SB216763 abrogated FTY720-induced apoptosis and allowed expansion of $CFSE^{max}$/CD34+ cells (FIG. 5D). Thus, β-catenin inhibition is essential for the detrimental effect of FTY720 on quiescent Ph+ HSC survival/self-renewal.

Figure 6:
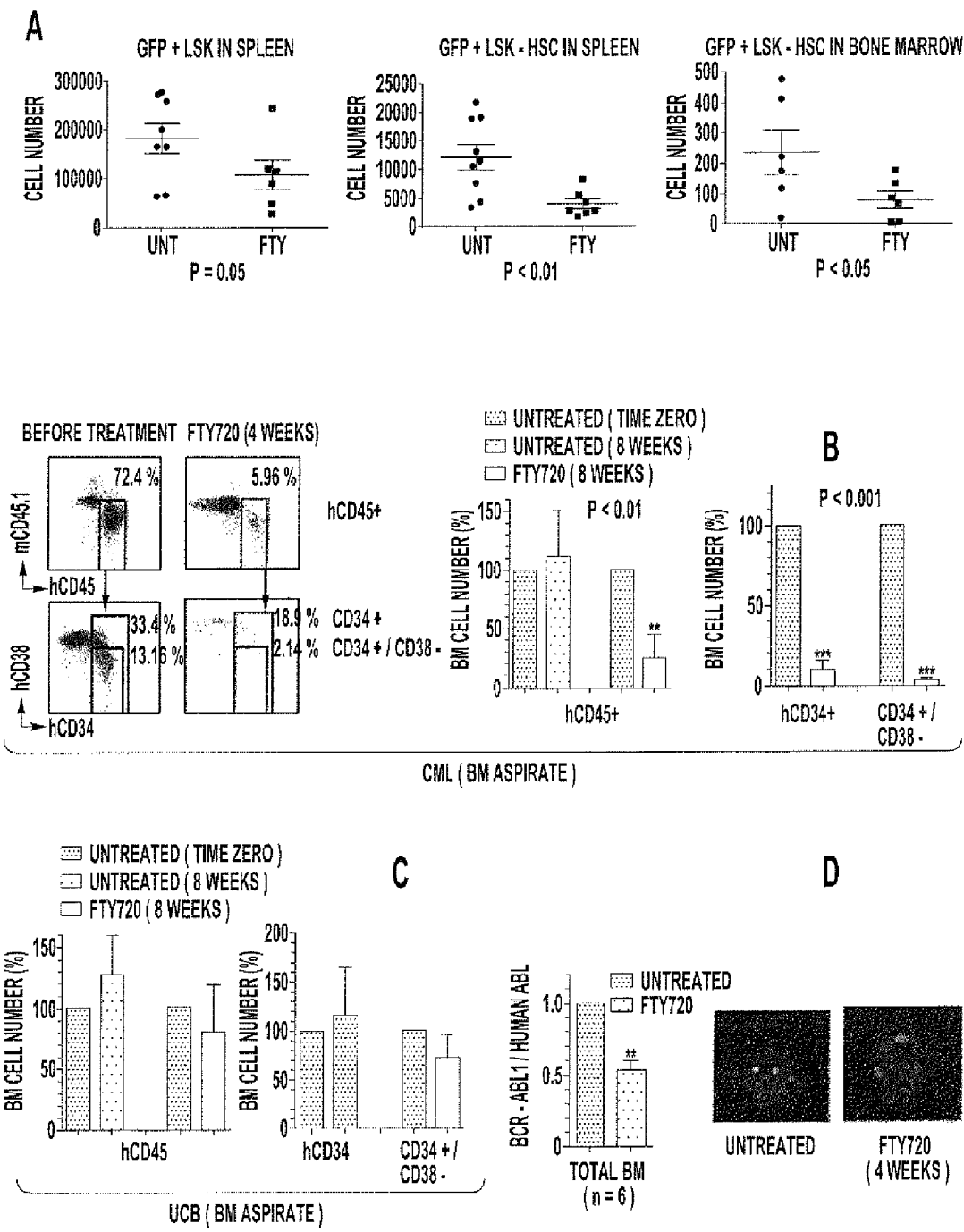
FIG. 6 provides dot plots, shows FTY720 suppresses mouse BCR-ABL1$^+$ LT-HSC and human Ph$^+$ stem and progenitor cell survival in vivo. (A): Dot plots show the in vivo effect of FTY720 (4 weeks) on the absolute numbers of GFP$^+$ (leukemic) LSK and LT-HSC in mice transplanted with leukemic BM cells from transgenic SCLtTA/BCR-ABL1/GFP mice; Student's t-test. (B&C): Flow plots (left) show the percentage of human (hCD45$^+$) cells, hCD34$^+$ progenitors and hCD34$^+$/CD38$^-$ HSC-enriched cell fraction in a representative CML xenotransplanted NSG mouse before and after 4 weeks of FTY720 treatment. Bar graphs show levels of hCD45$^+$, hCD34$^+$ and hCD34$^+$/CD38$^-$ cells in BM aspirated at time of engraftment (time 0: dark grey bars) and after 8 weeks in untreated (grey bars) and FTY720-treated (light grey bars) NSG mice (8-10 mice per group) intrafemorally transplanted with CD34$^+$ cells from CML-BC (B, right) patients (n=3) and UCB (C) donors (n=3). (D): Graph shows qRT-PCR-mediated analysis of BCR-ABL1 transcripts, expressed as BCR-ABL1 to human ABL1 ratio, in BM aspirates of CML-engrafted mice before and after FTY720 treatment (left); the microphotographs (right) show an interphase FISH field for BCR-ABL1 on FACS-sorted hCD45$^+$ cells from BM aspirates of untreated and 4-week FTY720-treated mice. Student's t-test was used to assess significance.

FTY720 suppresses leukemic HSC survival in vivo. In the first set of experiments, FTY720 (4-week treatment) reduced GFP+ (leukemic) LSK by ≥50% and splenic and/or BM GFP+ LT-HSC by ≥70% in congenic recipients transplanted with GFP+ total BM (n=16) or LSK (n=13) cells from SCLtTA/BCRABL1/GFP mice (FIG. 6A). Moreover, leukemic engraftment was observed in 25% and 83% of secondary recipients that received BM from FTY720- and vehicle-treated mice, respectively (Table I, Exp 1). Limiting dilution analysis showed that FTY720 reduced of ~80% the frequency of leukemic LTHSCs (Table I, Exp. 2).

TABLE I

| Experiment | Cell Dose in 2nd recipients | Engraftment-positive at 16 weeks (>0.1% GFP+) | |
|---|---|---|---|
| | | Untreated | FTY720 |
| #1 | 2,000,000 | 5/6 | 2/8 |
| #2 | 2,000,000 | 8/8 | 5/7 |
| | 1,000,000 | 7/7 | 3/7 |
| | 500,000 | 4/8 | 0/8 |
| | LT-HSC frequency | $2.23 \times 10^{-6}$ | $0.45 \times 10^{-6}$ |

In experiments with human Ph$^+$ primary cells, a reduction of ~83%, ~85% and ~97% in total hCD45$^+$ cells, CD45$^+$/CD34$^+$ progenitors and CD45$^+$/CD34$^+$/CD38$^-$ HSCs (P<0.001), respectively, was evident after 4 and 8 weeks of FTY720 treatment in BM of NSG mice (8-10 mice/group) engrafted with CML (n=3) CD34$^+$ BM cells (FIG. 6B). Likewise, Ph$^+$ hCD45$^+$/CD33$^+$ myeloid cells were also reduced. Interestingly, the comparable hCD45$^+$ cell numbers in untreated CML mice at engraftment (time 0) and after 8 weeks (FIG. 6B), the significant decrease in BCR-ABL1 transcripts (BCR-ABL1/hAbl1) and presence of mostly Ph$^-$ but not Ph$^+$ hCD45$^+$ cells in BM of FTY720-treated animals transplanted with a CML-BC sample containing a ~25% Ph– metaphases (FIG. 6D), is indicative of an expansion of normal hCD45$^+$ cells which are not target of FTY720. Accordingly, FTY720 did not exert noteworthy effects on identical human BM cell fraction from NSG mice engrafted with UCB (n=3) CD34$^+$ cells but, as expected, it reduced numbers of circulating B-(CD19$^+$) and T-(CD3$^+$) cells (FIG. 6C). Thus, FTY720 markedly and selectively reduces the number of leukemic HSCs and progenitors responsible for CML emergence, maintenance and relapse both in vitro and in vivo.

Discussion

The notion that tyrosine kinase inhibitors (TKIs) do not kill quiescent Ph$^+$ HSCs because BCR-ABL1 activity is dispensable for Ph$^+$ HSC survival, suggests that other aberrantly regulated signals contribute to TKI-resistance. Pellicano et al., Current hematologic malignancy reports; 6: 82-7 (2011). The data support the hypothesis that BCR-ABL1 expression per se is required for Ph$^+$ stemness. The inventors showed that BCR-ABL1 levels, but not its kinase activity, are substantially higher in quiescent than in dividing HSCs, and that this upregulation is not transcriptional but likely relies on events stabilizing BCR-ABL1 in a nearly, albeit not totally, inactive state. Indeed, a similar pattern of BCR-ABL1 expression was also observed in leukemic HSCs and progenitors from BCR-ABL 1-transgenic mice. Schemionek et al., Blood, 115: 3185-95 (2010). Moreover, the use of BCR-ABL1 shRNA and kinase-deficient BCR-ABL1 mutant indicate that BCRABL1 expression in quiescent HSCs leads to JAK2 activation, and suggest that JAK2 likely stabilizes BCR-ABL1 and controls Ph$^+$ quiescent HSC survival/self-renewal (FIG. 5E). Accordingly, JAK2 activity was higher in CML than normal quiescent HSCs; JAK2 inhibition reduced survival/self-renewal and BCR-ABL1 activity in Ph$^+$ HSCs; and, levels of BCR-ABL1 and its JAK2-dependent Y177 phosphorylation decrease upon JAK2 downregulation in CD34$^+$ progenitors. Samanta et al., Leukemia; 25: 463-72 (2011). These findings indicate that JAK2 stabilizes BCR-ABL1 and utilizes it as a scaffold to control survival signals. Strengthening the importance of this BCR-ABL1/JAK2 interplay in Ph$^+$ HSCs, the inventors showed that JAK2 activity is necessary for the BCR-ABL1 kinase-independent induction, nuclear localization and transcriptional activity of β-catenin. Accordingly, retroviral BCR-ABL1 transduction/transplantation studies with β-catenin wild-type and null cells suggested the importance of β-catenin for survival/self-renewal of dividing BCR-ABL1$^+$ stem/progenitors and revealed that BCR-ABL1 induces β-catenin in an imatinibin-sensitive manner. The existence of a JAK2-β-catenin pathway requiring BCR-ABL1 expression but not activity does not contradict the BCR-ABL1 kinase-dependent β-catenin induction/stabilization observed in CML progenitors. Coluccia et al., Embo J; 26: 1456-66 (2007). In fact, TKI sensitivity is a characteristic of dividing but not quiescent CML cells. In this regard, the inventors reported that induction of the JAK2-SET pathway and PP2A inhibition occurs in a BCR-ABL1 kinase-dependent manner in CD34+ CML progenitors and BCR-ABL1$^+$ lines. Samanta et al., Oncogene, 28: 1669-81 (2009). Conversely, here the inventors showed that the SET-mediated PP2A inactivation is essential for survival/self-renewal of quiescent Ph$^+$ HSCs and maintenance of an active JAK2-β-catenin pathway, and that PP2A is suppressed in Ph$^+$ HSCs in a BCR-ABL1 kinase-independent JAK2-dependent manner. This is understandable, as JAK2 and PP2A negatively regulate each other (FIG. 4E) in hematopoietic progenitors. Yokoyama et al., J Interferon Cytokine Res, 21: 369-78 (2001). Thus, PP2A inactivation has a relevant role in the maintenance of Ph$^+$ HSC survival/self-renewal in TKI-treated CML patients.

Provided herein is evidence that FTY720 is not toxic to normal HSCs while it markedly impairs self-renewal and survival of TKI-resistant quiescent Ph$^+$ HSCs. Surprisingly, these effects were not due to BCR-ABL1 inactivation as had been reported in Ph$^+$ progenitors, (Neviani et al., J Clin Invest; 117: 2408-21 (2007)) but were mediated by the PP2A-induced inactivation of JAK2 and β-catenin. This conclusion is supported by the fact that FTY720-dependent restoration of PP2A activity in leukemic progenitors is accompanied by decreased PP2A$_C^{Y307}$ phosphorylation, which represents a JAK2-dependent direct mechanism of PP2A inactivation. Likewise, the FTY720-induced β-catenin inhibition could depend on both JAK2 inhibition and/or the direct PP2A effect on β-catenin and its destruction complex (e.g. GSK-3β). Patturajan et al., Cancer Cell; 1: 369-79 (2002) The dependence of FTY720 anti-leukemic HSC activity on PP2A reactivation and inhibition of β-catenin is also supported by the counteracting effect of the PP2A inhibitor okadaic acid on FTY720 and TG101348, and of GSK-30β inhibitors on FTY720. Of note, JAK2 inhibitors (Lasho et al., Leukemia, 22: 1790-2 (2008)) might represent an attractive way to halt the survival of quiescent Ph$^+$ HSCs, especially for their ability to inhibit β-catenin. However, the toxicity of TG101348 to normal CD34$^+$ progenitors, when used at concentrations that impair PH$^+$ HSC survival (FIG. 4B), argue against its use in CML eradication trials. Conversely, FTY720 has strong in vitro and in vivo pro-apoptotic activities towards leukemic stem/progenitor cells with a desirable nontoxic profile in ex vivo primary cells and long-term animal studies if one excludes its immunosuppressive activity, which can be avoided by using FTY720-derivatives that kill leukemic HSCs and progenitors without inducing lymphopenia. By contrast, FTY720-phosphate did not induce PP2A activity (Roberts et al., Cancer Res; 70: 5438-47 (2010)) and apoptosis of Ph$^+$ HSCs, indicating that FTY720 phosphorylation, albeit required for the effects in Multiple Sclerosis (MS), is dispensable for its anti-leukemic activity. In fact, the evidence that most of the intracellular FTY720 in myeloid cells remains non-phosphorylated and its strong anti-leukemic activity argues with the notion that FTY720 is mostly in its phosphorylated form when administered in vivo.

In conclusion, CML cure is potentially achievable at the stem cell level with PP2A-activating drugs (PADs: FTY720 and its non-immunosuppressive derivatives). Thus, TKI-treated CML patients in CMR may be spared from lifelong therapy. Moreover, this and the inventors' previous reports strongly support testing PADs in Ph+ patients. Importantly, these drugs seemingly have a high therapeutic index as they selectively activate PP2A in leukemic HSCs/progenitors without adverse effects on normal hematopoiesis. Furthermore, because of their wider implications on other molecular networks (FIG. 5E) which control $Ph^+$ stemness and are regulated by PP2A, the clinical importance of our findings is not limited to CML but can be extended to other stem cell malignancies The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the compounds of the invention are effective, the inventors are not bound by theories described herein. The invention is not limited to the exact details shown and described, for variations obvious to one skilled in the art will be included within the invention defined by the claims.

What is claimed is:

1. A method of inhibiting the growth of leukemic hematopoietic stem cells in a subject with leukemia, comprising administering a therapeutically effective amount of a composition including a compound of Formula II:

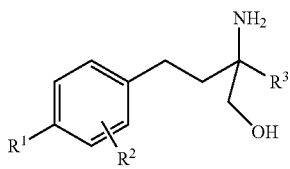

II wherein $R^1$ is a $C_6$-$C_{12}$ alkyl or $C_6$-$C_{12}$ alkoxy group;
$R^2$ is independently selected from the group consisting of hydrogen, methoxy, and hydroxyl; and
$R^3$ is a an alkyl or cycloalkyl group; or a pharmaceutically acceptable salt thereof.

2. The method of claim 1, wherein the leukemia is a Ph+ leukemia.

3. The method of claim 2, wherein the Ph+ leukemia is chronic myelogenous leukemia.

4. The method of claim 1, wherein the composition has a cytotoxic effect on leukemic hematopoietic stem cells.

5. The method of claim 1, wherein $R^1$ is $C_6$-$C_{12}$ alkyl.

6. The method of claim 1, wherein $R^1$ is $C_6$-$C_{12}$ alkoxy.

7. The method of claim 1, wherein $R^2$ is hydrogen and $R^3$ is selected from the group consisting of propyl, isopropyl, isobutyl, cyclopropyl methyl, and cyclobutyl methyl.

8. The method of claim 1, wherein $R^1$ is $C_8$ alkyl or $C_8$ alkoxy.

9. The method of claim 8, wherein $R^2$ is hydrogen and $R^3$ is selected from the group consisting of propyl, isopropyl, isobutyl, cyclopropyl methyl, and cyclobutyl methyl.

10. The method of claim 8, wherein the compound has the structure

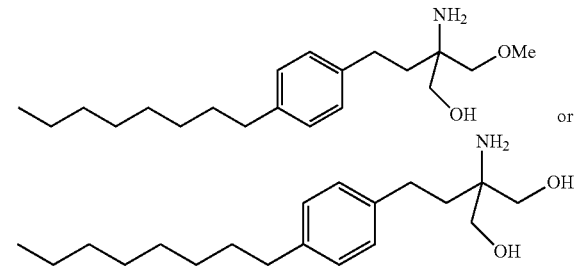

11. The method of claim 8, wherein the compound has the structure

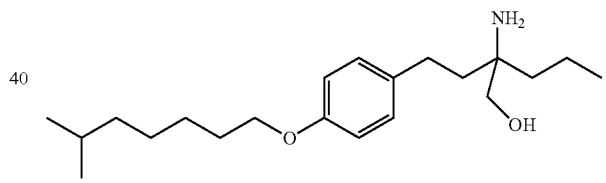

* * * * *

UNITED STATES PATENT AND TRADEMARK OFFICE
CERTIFICATE OF CORRECTION

PATENT NO. : 9,220,706 B2  
APPLICATION NO. : 14/404496  
DATED : December 29, 2015  
INVENTOR(S) : Danilo Perrotti and Paolo Neviani Page 1 of 1

It is certified that error appears in the above-identified patent and that said Letters Patent is hereby corrected as shown below:

In the Specification

Column 1, Lines 16-19 replace the Government Support Clause with:
--This invention was made with government support under grant number CA095512 awarded by the National Institutes of Health. The government has certain rights in the invention.--

Signed and Sealed this
Twenty-second Day of September, 2020

Andrei Iancu
*Director of the United States Patent and Trademark Office*